(12) United States Patent
Smith et al.

(10) Patent No.: US 7,959,162 B2
(45) Date of Patent: Jun. 14, 2011

(54) RELEASING INSTRUMENT HOLDER AND METHOD OF OPERATING THE INSTRUMENT HOLDER

(75) Inventors: Kevin Smith, Coral Gables, FL (US);
Derek Deville, Miami, FL (US);
Thomas Bales, Coral Gables, FL (US);
Carlos Rivera, Cooper City, FL (US);
Matthew Palmer, Miami, FL (US);
Max Mendez, Miami, FL (US); Michael Kirk, Miami, FL (US)

(73) Assignee: Syntheon, LLC, Miami, FL (US)

( * ) Notice: Subject to any disclaimer, the term of this patent is extended or adjusted under 35 U.S.C. 154(b) by 983 days.

(21) Appl. No.: 11/828,424

(22) Filed: Jul. 26, 2007

(65) Prior Publication Data

US 2009/0026682 A1    Jan. 29, 2009

(51) Int. Cl.
*B23B 31/16* (2006.01)
(52) U.S. Cl. ............... 279/74; 279/75; 279/82; 279/904
(58) Field of Classification Search .................... 279/75, 279/74, 82, 904
See application file for complete search history.

(56) References Cited

U.S. PATENT DOCUMENTS

| 4,199,160 A * | 4/1980 | Bent ............................... 279/30 |
| 5,011,344 A * | 4/1991 | Johnson ........................ 408/240 |
| RE37,358 E * | 9/2001 | Del Rio et al. .................. 606/80 |
| 6,382,636 B1 * | 5/2002 | Walker ............................ 279/60 |
| 6,786,685 B2 * | 9/2004 | Schaub et al. ............... 408/240 |
| 7,040,630 B2 * | 5/2006 | Huggins et al. ................. 279/62 |
| 7,448,870 B2 * | 11/2008 | Ma tre ......................... 433/114 |
| 7,645,138 B2 * | 1/2010 | Boinot .......................... 433/128 |
| 7,707,916 B2 * | 5/2010 | Pirseyedi ....................... 81/128 |

* cited by examiner

*Primary Examiner* — Eric A Gates
*Assistant Examiner* — Bayan Salone
(74) *Attorney, Agent, or Firm* — Mayback & Hoffman, P.A.; Gregory L. Mayback; Katie M. Blakley (57) ABSTRACT

An automatically releasing instrument holder includes a grip to be held by an operator for guiding an instrument, an actuator to be activated by the operator and a biasing device exerting a force. A clamp is moved by the actuator toward the instrument against the force of the biasing device and is moved by the biasing device away from the instrument upon releasing the actuator. A method for operating the instrument holder is also provided.

20 Claims, 14 Drawing Sheets

RELEASING INSTRUMENT HOLDER AND METHOD OF OPERATING THE INSTRUMENT HOLDER

BACKGROUND OF THE INVENTION

1. Field of the Invention

The invention relates to an automatically releasing instrument holder. The invention also relates to a method of operating the instrument holder. An endoscope or a colonoscope is, in particular, contemplated as the instrument.

2. Description of the Related Art

Prior art devices and therefore methods of operating the same have been complicated and required separate manipulations to engage and release the instrument and only engage it with a set, non-adjustable force.

SUMMARY OF THE INVENTION

It is accordingly an object of the invention to provide an automatically releasing instrument holder and a method of operating the instrument holder, which overcome the hereinafore-mentioned disadvantages of the heretofore-known devices and methods of this general type and which are simple to construct and operate, automatically release upon disengagement by the operator of the device, such as a surgeon, and allow infinite adjustment.

With the foregoing and other objects in view there is provided, in accordance with the invention, an automatically releasing instrument holder, comprising a grip to be held by an operator for guiding an instrument, an actuator to be activated by the operator, and a biasing device exerting a force. A clamp is moved by the actuator toward the instrument against the force of the biasing device and is moved by the biasing device away from the instrument upon releasing the actuator. The biasing device may be a spring, and the actuator may be a trigger being pivoted away from the grip by the spring and being pivoted toward the grip by the operator for engaging the instrument with the clamp. The spring is biased between a nose and the cam. Therefore, a simple, easily operated, reliable and automatically releasing instrument holder is provided. An important advantage of the instrument holder according to the invention is that the actuator and the biasing device allow infinite adjustment of contact between the clamp and the instrument by the operator.

In accordance with another feature of the invention, the clamp includes a plurality of clamping shoes for surrounding the instrument. A cam is moved by the trigger for displacing the clamping shoes toward the instrument and is moved by the spring for displacing the clamping shoes away from the instrument. A cam ring is disposed within the cam. Cam lock springs are each being disposed between a respective two of the clamping shoes. The clamping shoes, for example three in number, provide equalized force distribution against the instrument from all radial directions for secure gripping without damage to the instrument.

In accordance with a further feature of the invention, the cam has a cam surface on which ball bearings ride toward and away from the clamping shoes upon movement of the cam. A clamp body has holes formed therein in which the ball bearings move toward and away from the clamping shoes. The clamping shoes each have a protrusion being engaged by a respective one of the ball bearings. This feature provides infinite adjustment between clamped and released positions of the shoes, allowing the operator to chose and feel the force to be exerted.

In accordance with an added feature of the invention, there is provided a grip tube extended through the grip, one dowel pin on which the trigger pivots on the grip, and another dowel pin disposed between the clamp body and the grip tube, perpendicular to the one dowel. Set screws are disposed between the clamp body and the grip tube. The dowel pins and the set screws allow balanced support for the moving and stationary parts of the instrument holder.

With the objects of the invention in view, there is also provided a method for operating an automatically releasing instrument holder. The method comprises guiding an instrument in a grip to be held by an operator, providing an actuator or trigger to be activated by the operator, exerting a force against activation of the actuator with a biasing device or spring, and providing a clamp or clamping shoes for engaging the instrument. The actuator is activated by the operator to move the clamp toward the instrument against the force of the biasing device. The clamp is moved away from the instrument with the biasing device upon releasing the actuator.

Other features which are considered as characteristic for the invention are set forth in the appended claims.

Although the invention is illustrated and described herein as embodied in an automatically releasing instrument holder and a method of operating the instrument holder, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
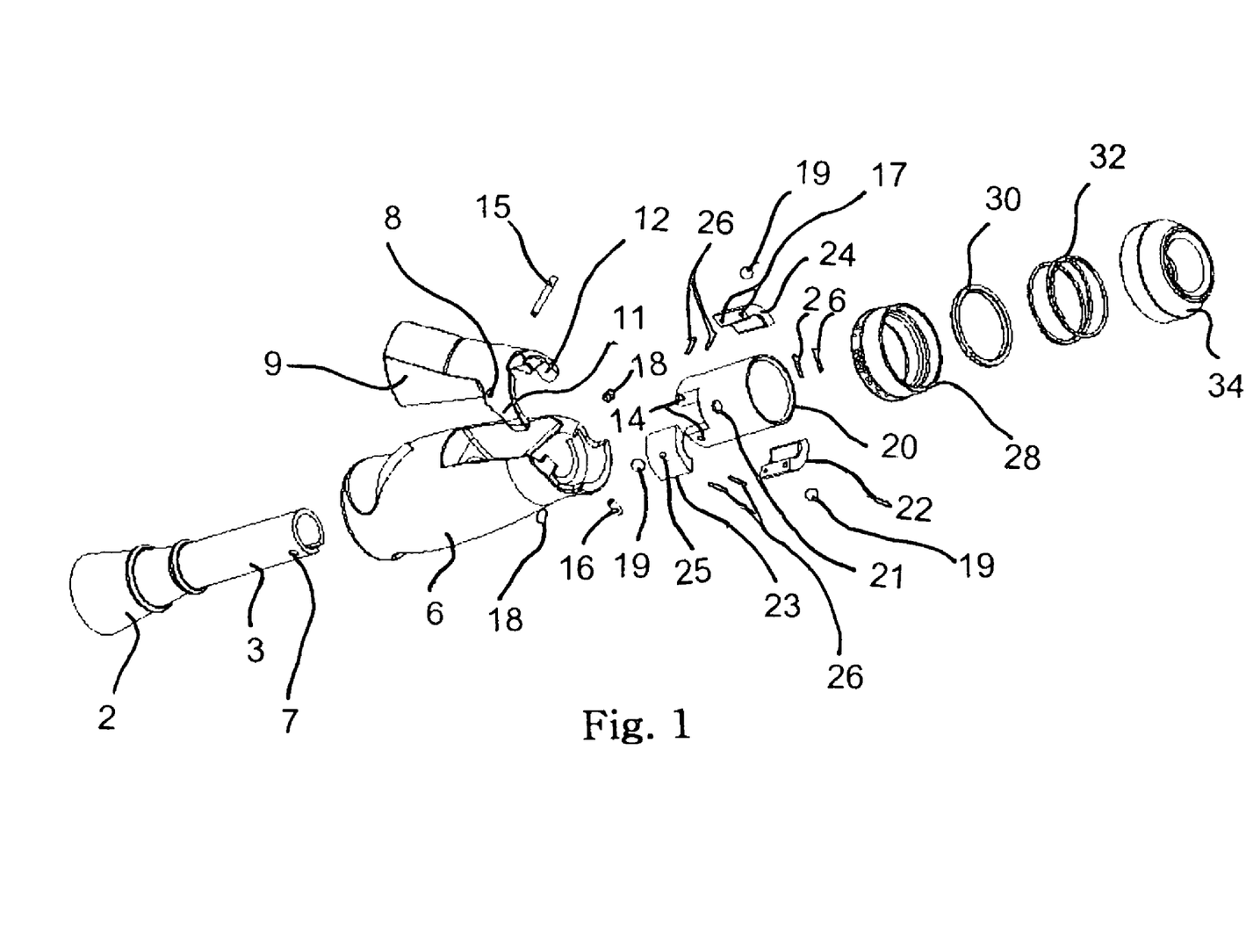
FIG. 1 is a diagrammatic, exploded perspective view of an instrument holder according to the invention.

Referring now to the figures of the drawings in detail and first, particularly, to FIG. 1 thereof, there is seen an exploded perspective view of an automatically releasing instrument holder according to the invention. The instrument holder includes a grip tube 2 to be slid inside a grip 6 for manipulation by an operator. A manual actuator in the form of a trigger 9 is to be hinged on the grip 6 by a dowel pin 15 passing through holes 8 in the trigger 9, only one of which is shown, and corresponding non-illustrated holes in the grip 6. The trigger 9 also has arms 11, 12 which pivot about the dowel pin 15. When assembled, an extension 3 of the grip tube 2 extends through the grip 6 and partly through a clamp body 20. Two set screws 18 are each engaged in a respective threaded opening 14 in the clamp body 20. Each set screw 18 engages a respective protrusion 7 on the extension 3, only one of which is shown. A clamp in the form of three clamping shoes 22, 23, 24 are held within the clamp body 20 and are biased against one another by cam lock springs 26 which extend into blind bores 17 formed in pairs in the clamping shoes. The clamping shoes 22, 23, 24 each have a protrusion 25 aligned with a respective hole 21 in the clamp body 20. Only one of the protrusions 25 and holes 21 are shown. Ball bearings 19 are each to be placed in a respective one of the holes 21 for contacting a respective one of the protrusions 25. Another dowel pin 16 passes through non-illustrated holes in the clamp body 20 and the extension 3, perpendicular to the dowel 15. A cam 28, a cam ring 30 and a biasing device in the form of a spring 32 surround the clamp body 20. A nose 34 is slipped over the spring 32 and the cam ring 30.

Figure 2:
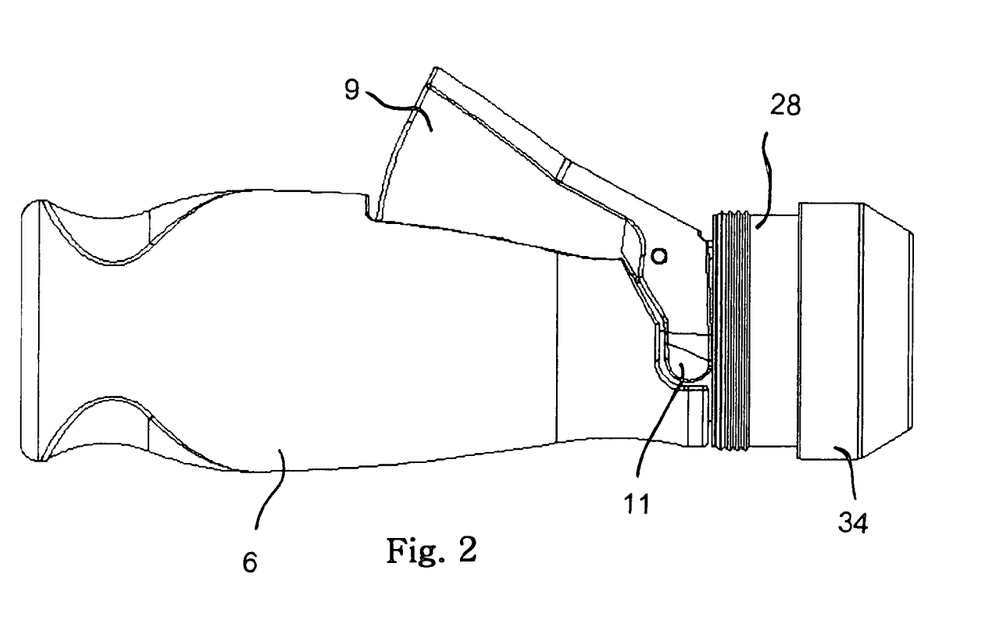
FIG. 2 is a side-elevational view of the instrument holder with a trigger released in an unlocked condition.
Figure 3:
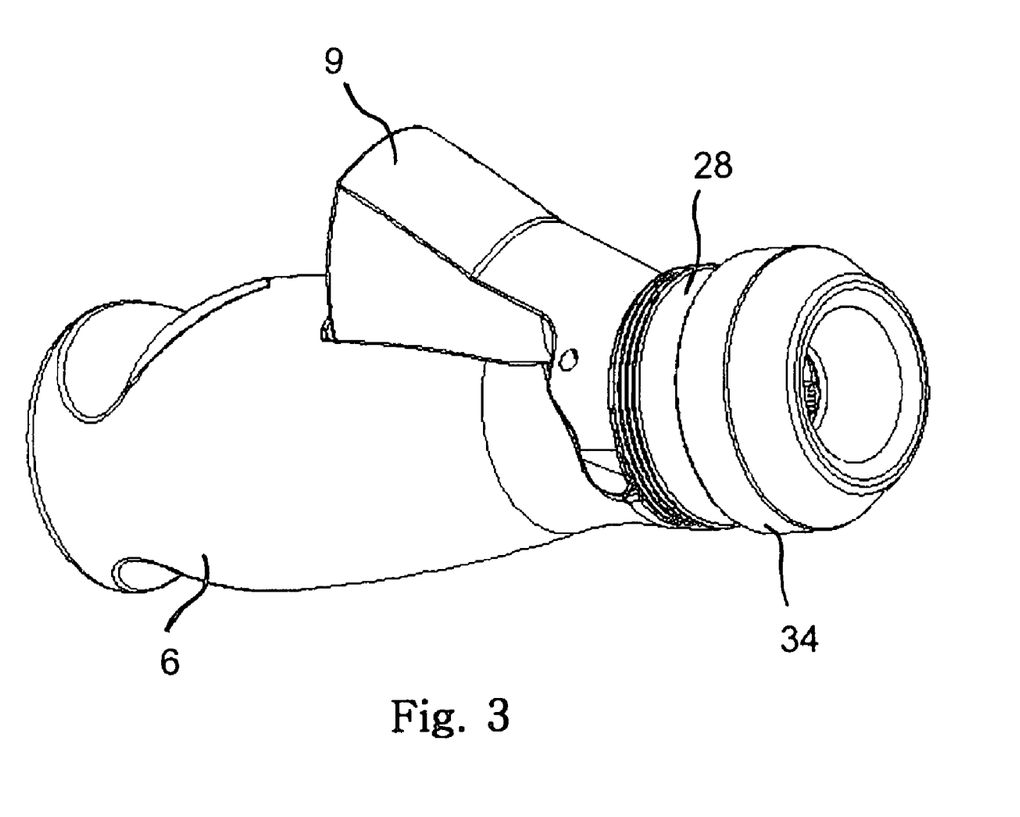
FIG. 3 is a perspective view of the instrument holder with the trigger released in the unlocked condition.
Figure 4:
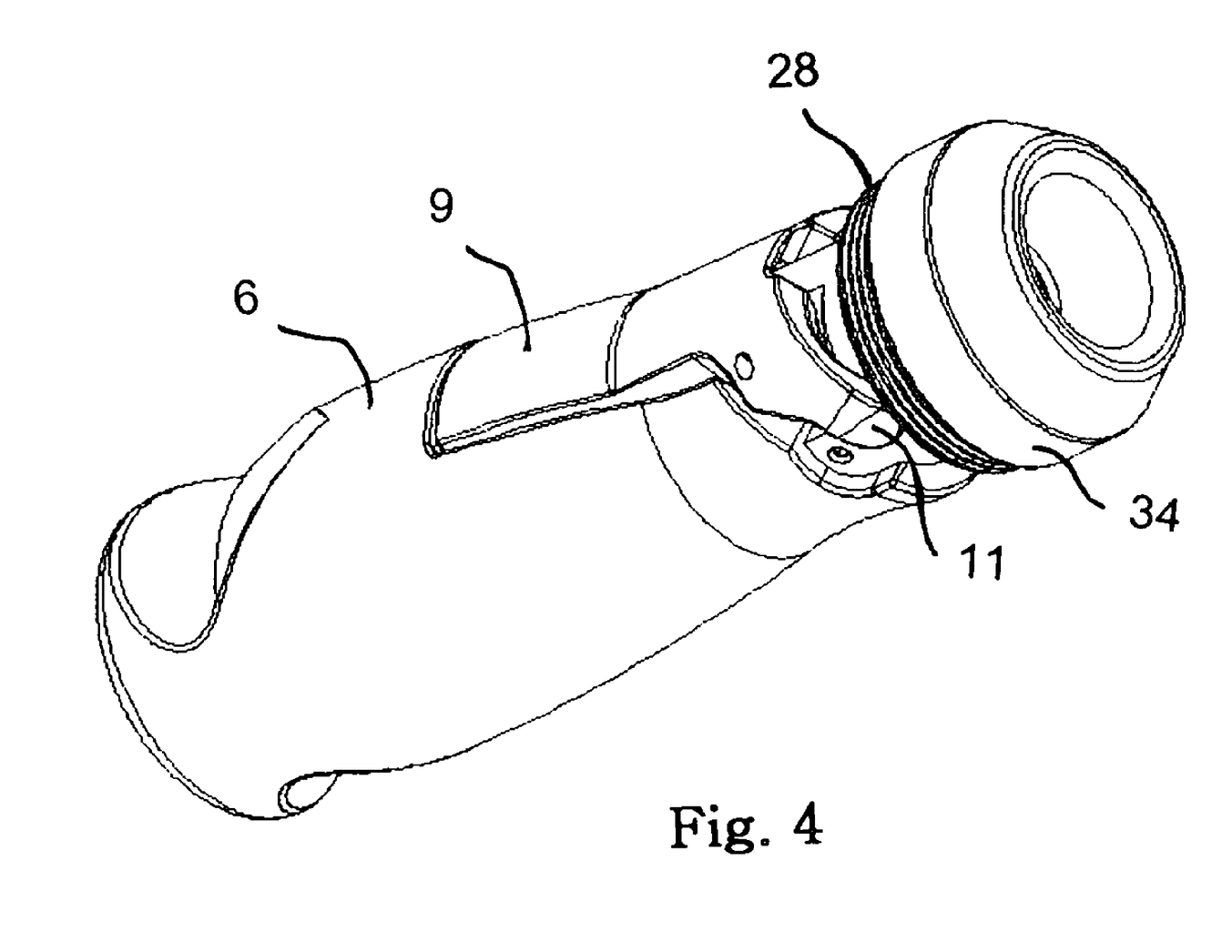
FIG. 4 is a perspective view of the instrument holder with the trigger depressed in the locked condition.
Figure 14:
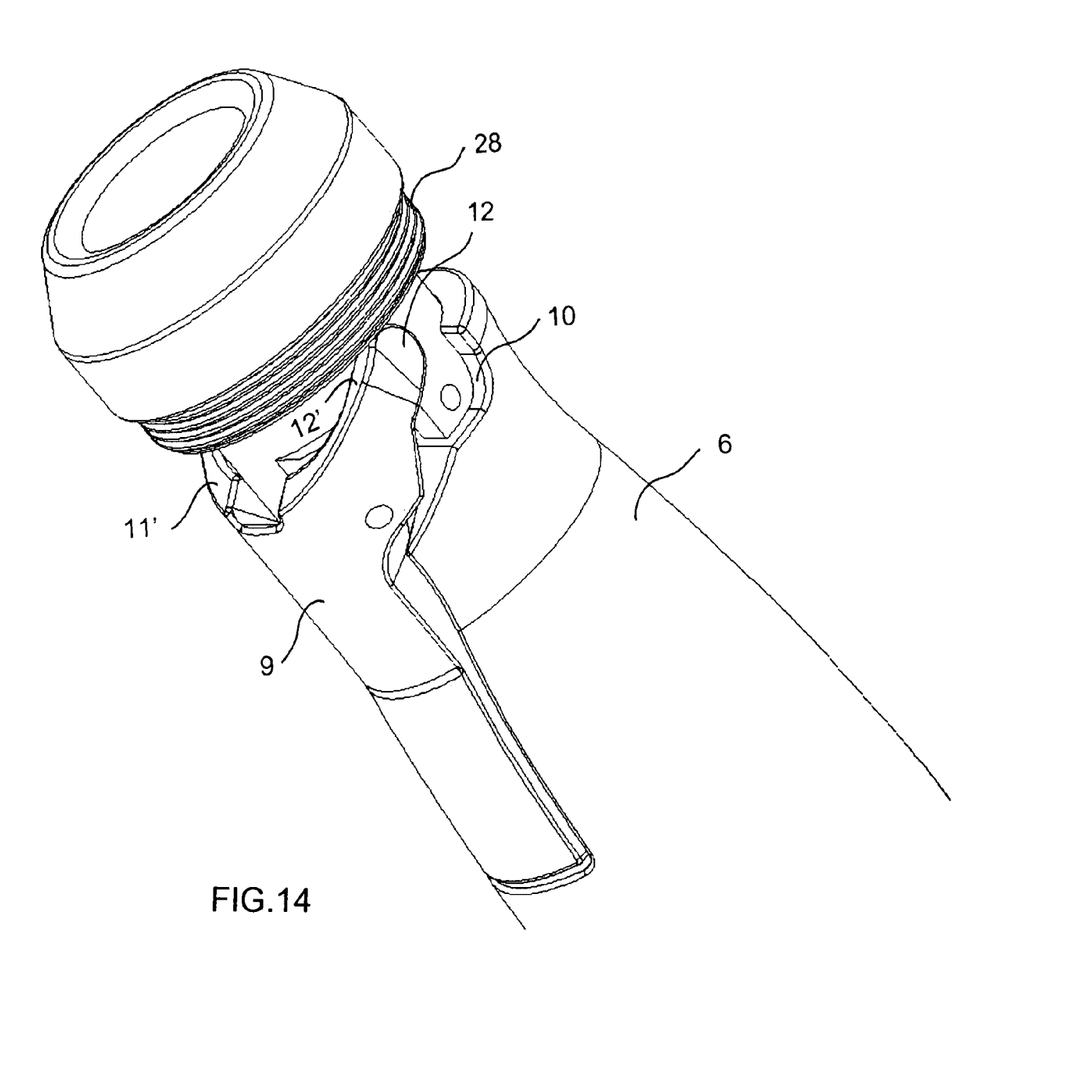
FIG. 14 is an enlarged, fragmentary, perspective view of the instrument holder with the trigger depressed in the locked condition.

FIGS. 2 and 3 illustrate the assembled instrument holder in respective elevational and perspective views, with the trigger 9 released and the nose 34 in an unlocked position, that is fully retracted towards the cam 28. In the perspective view of FIG. 4, the trigger 9 has been fully depressed by the operator to pivot about the dowel pin 15, so that the arms 11, 12 push the cam 28 toward the right in FIG. 4, that is distally. The perspective view of FIG. 14 shows a particularly clear illustration of the arms 11, 12 engaging the cam 28. It may be seen that the arms 11, 12 have engagement surfaces 11', 12', different parts of which engage the cam 28 during the stroke of the trigger 9 between the depressed and released positions. When the trigger 9 is released, the spring 32 pushes the cam 28 and the arms 11, 12 toward the left in FIG. 4, that is proximally, so that the trigger 9 is once again extended as in FIGS. 2 and 3 and the ends of the arms 11, 12 are seated against stops 10 on the grip 6, only one of which is shown in FIG. 14.

Figure 5:
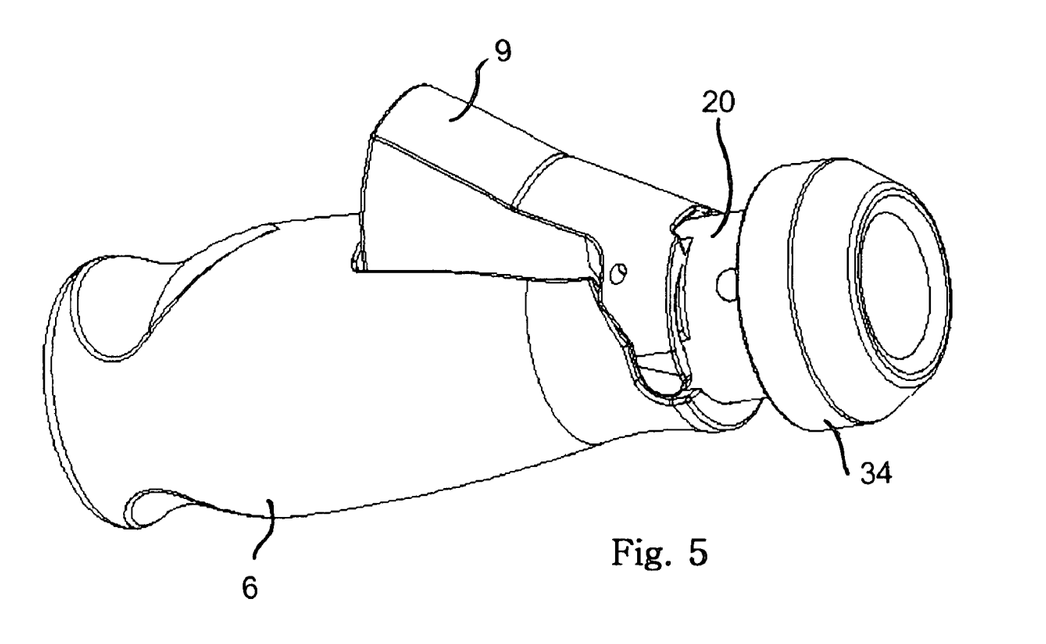
FIG. 5 is a perspective view of the instrument holder with the trigger released in the unlocked condition and a cam removed.
Figure 6:
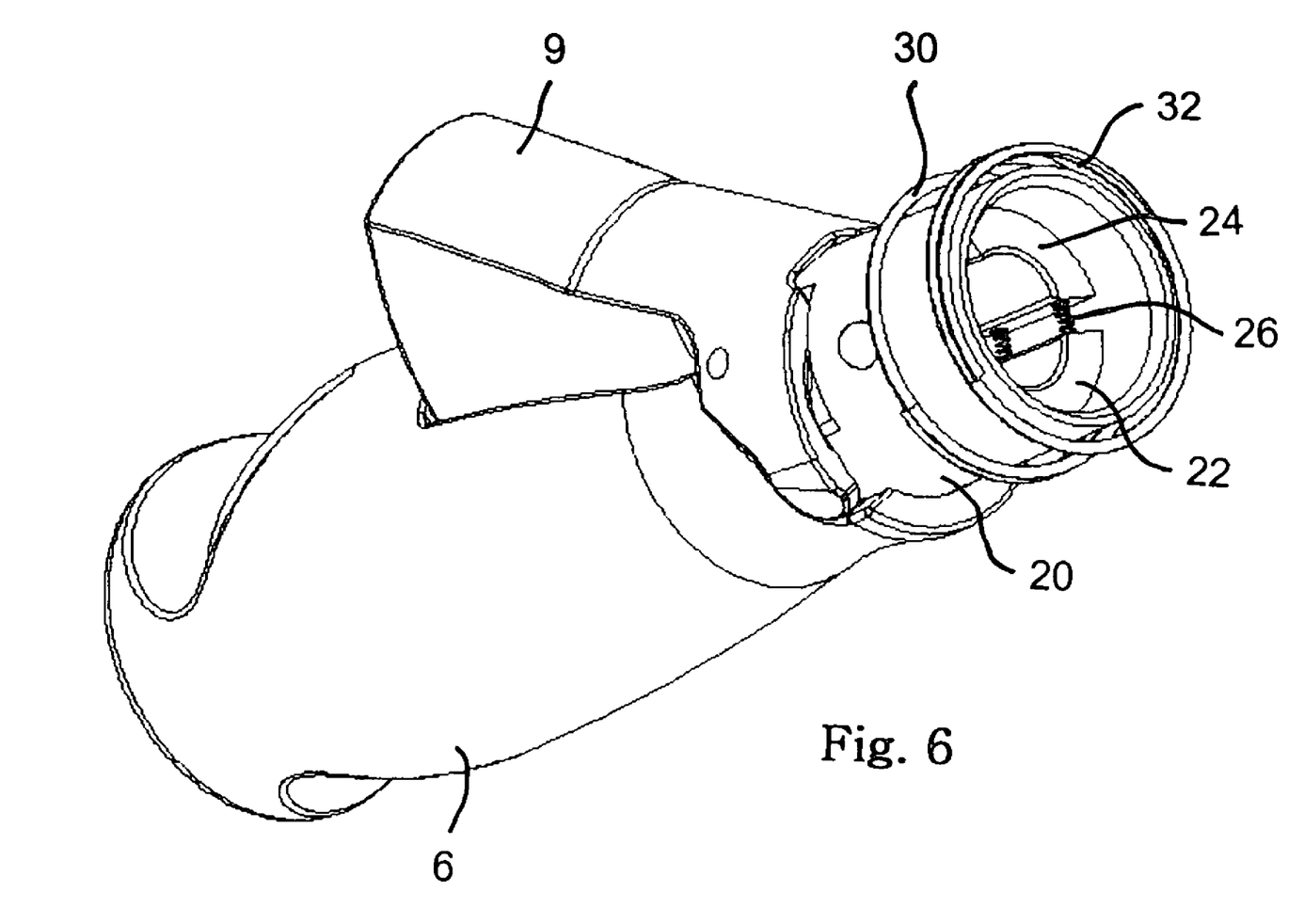
FIG. 6 is a perspective view of the instrument holder with the trigger released in the unlocked condition and with a nose removed.
Figure 7:
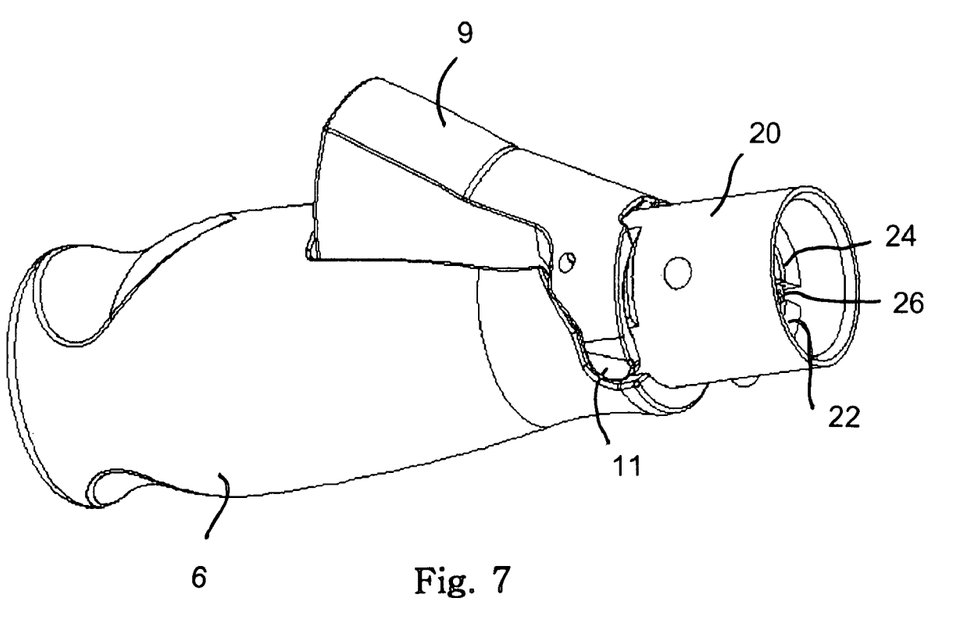
FIG. 7 is a perspective view of the instrument holder with the trigger released in the unlocked condition and with a spring and a cam ring removed.
Figure 8:
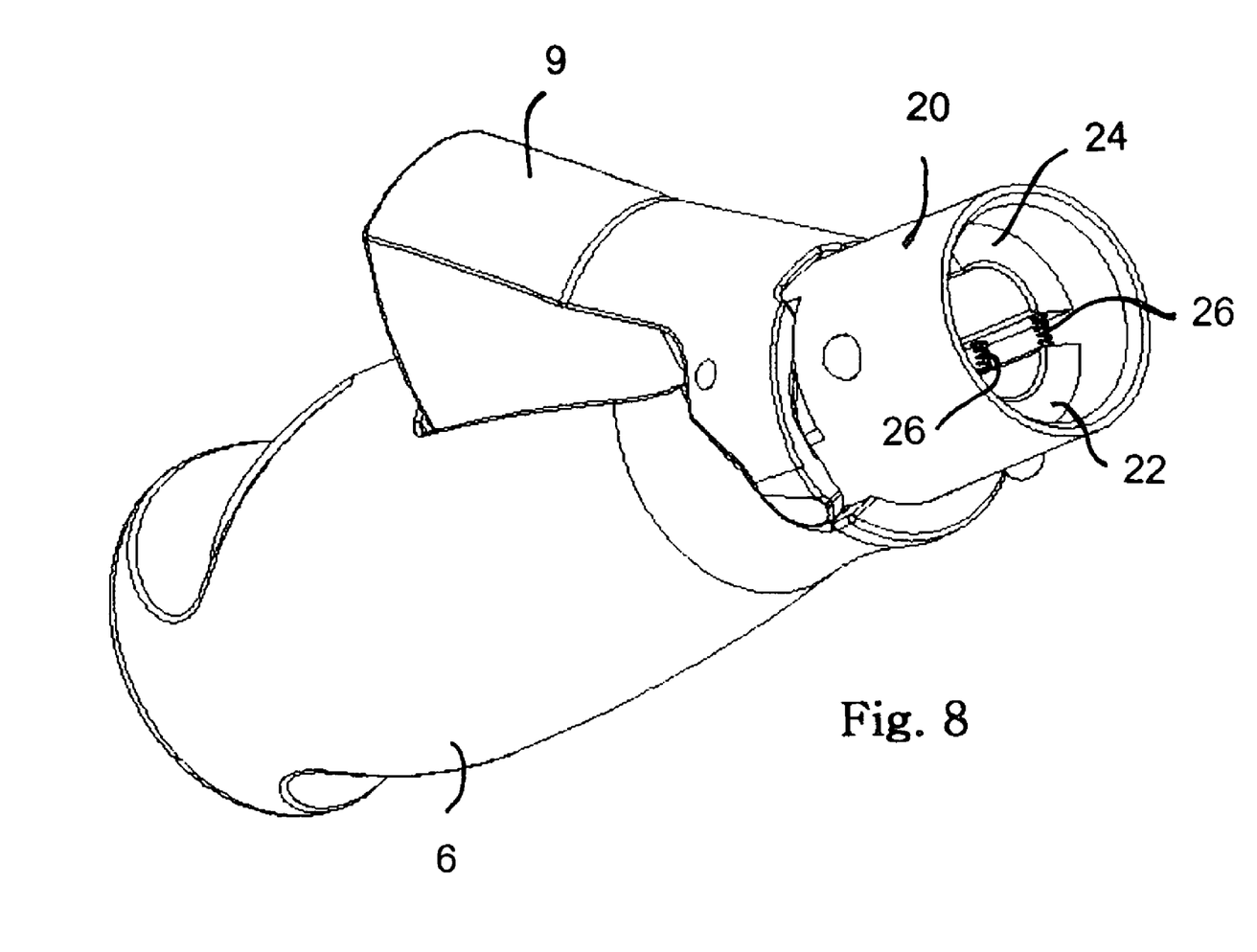
FIG. 8 is another perspective view similar to FIG. 7.
Figure 9:
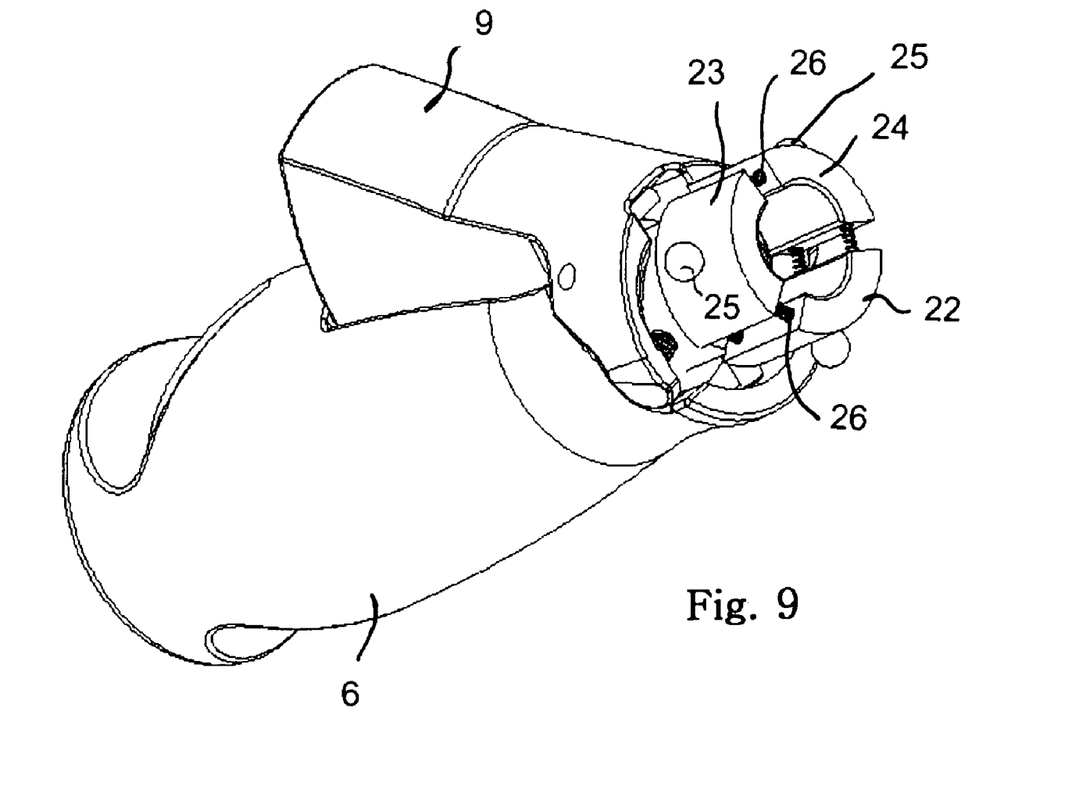
FIG. 9 is a perspective view of the instrument holder with the trigger released in the unlocked condition and with a clamp body removed.

In the perspective view of FIG. 5, the cam 28 has been removed to more clearly show the clamp body 20. In the perspective view of FIG. 6, the nose 34 has also been removed, to show the cam ring 30 and the spring 32 surrounding the clamp body 20. The perspective views of FIGS. 7 and 8 show portions of the clamping shoes 22, 24 and the cam lock springs 26 within the clamp body 20. In FIG. 9, the clamp body 20 has been removed to show all three clamping shoes 22, 23, 24 and several of the cam lock springs 26 and protrusions 25.

Figure 10:
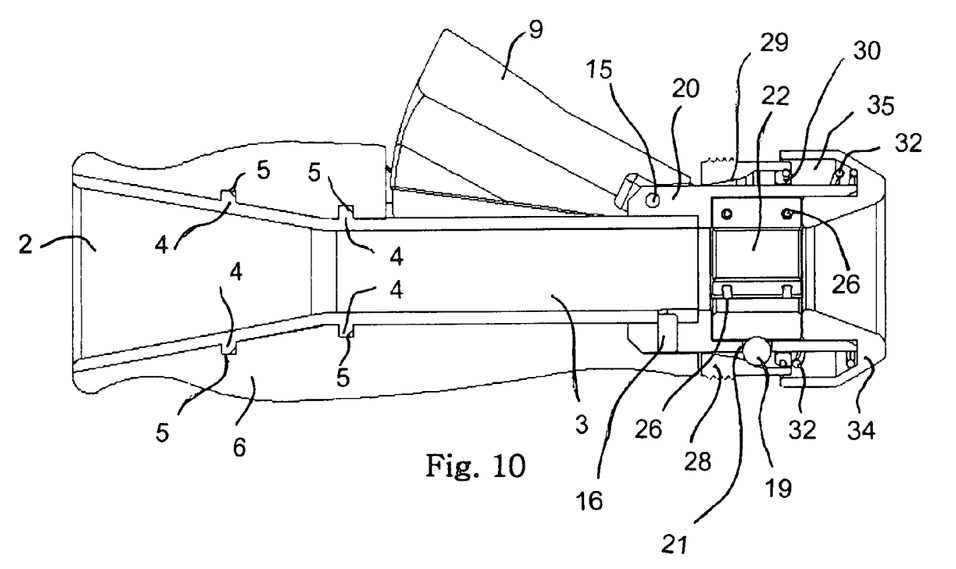
FIG. 10 is a longitudinal-sectional view of the instrument holder with the trigger released in the unlocked condition.

The longitudinal-sectional view of FIG. 10 shows the trigger 9 released and therefore in the unlocked condition. The dowel pin 15 interconnecting the trigger 9 and the grip 6 and the dowel pin 16 interconnecting the clamp body 20 and the extension 3, are seen as well. The cam ring 30 is seen as being disposed within the distal end of the clamp body 20. It may also be seen that the grip tube 2 and the extension 3 have beads 4 engaged in corresponding recesses 5 in the grip 6. FIG. 10 also illustrates an inner annular cam surface or ramp 29 of the cam 28. The above-mentioned three holes 21 formed in the clamp body 20 and three ball bearings 19 each being radially movable in a respective one of the holes 21, may be seen in FIG. 10 as well. Finally, FIG. 10 shows the spring 32 disposed in a cavity 35 within the nose 34. It may be seen that the spring 32 is biased between the nose 34 and the cam 28, so as to bias the cam to the left or proximally in FIG. 10. The non-illustrated protrusions 25 on the clamping shoes 22, 23, 24 are each radially aligned with a respective one of the ball bearings 19.

Figure 11:
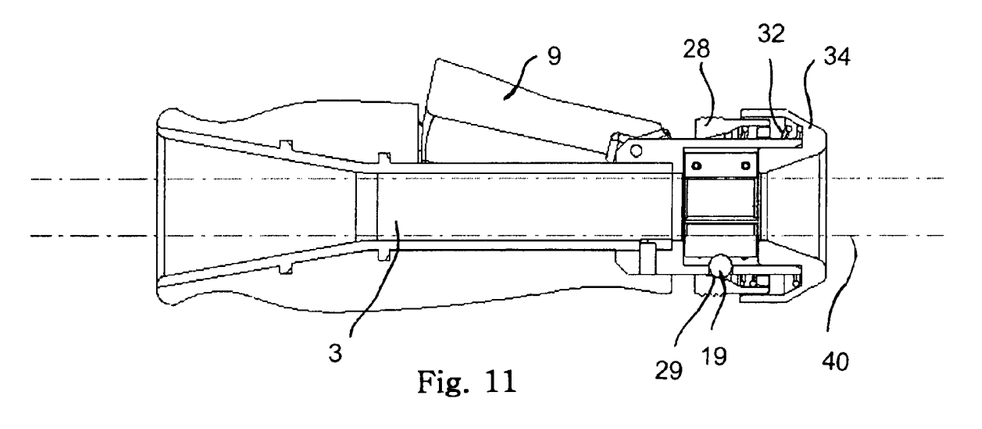
FIG. 11 is a longitudinal-sectional view of the instrument holder with the trigger partly depressed in a partly locked condition.

In the longitudinal-sectional view of FIG. 11, the trigger 9 has been partly depressed, so that the arms 11, 12 push the cam 28 distally, causing the cam surface 29 to engage the ball bearings 19 and push them radially inwardly in the holes 21 against the protrusions 25 on the clamping shoes 22, 23, 24. The clamping shoes 22, 23, 24 are in turn pushed radially inwardly against the force of the springs 26 and toward an instrument 40, such as an endoscope or a colonoscope. The instrument 40 protrudes from the proximal and distal ends of the instrument holder and passes through a hollow body formed by the grip tube 2, the clamp body 20, the clamping shoes 22, 23, 24 and the hollow nose 34.

Figure 12:
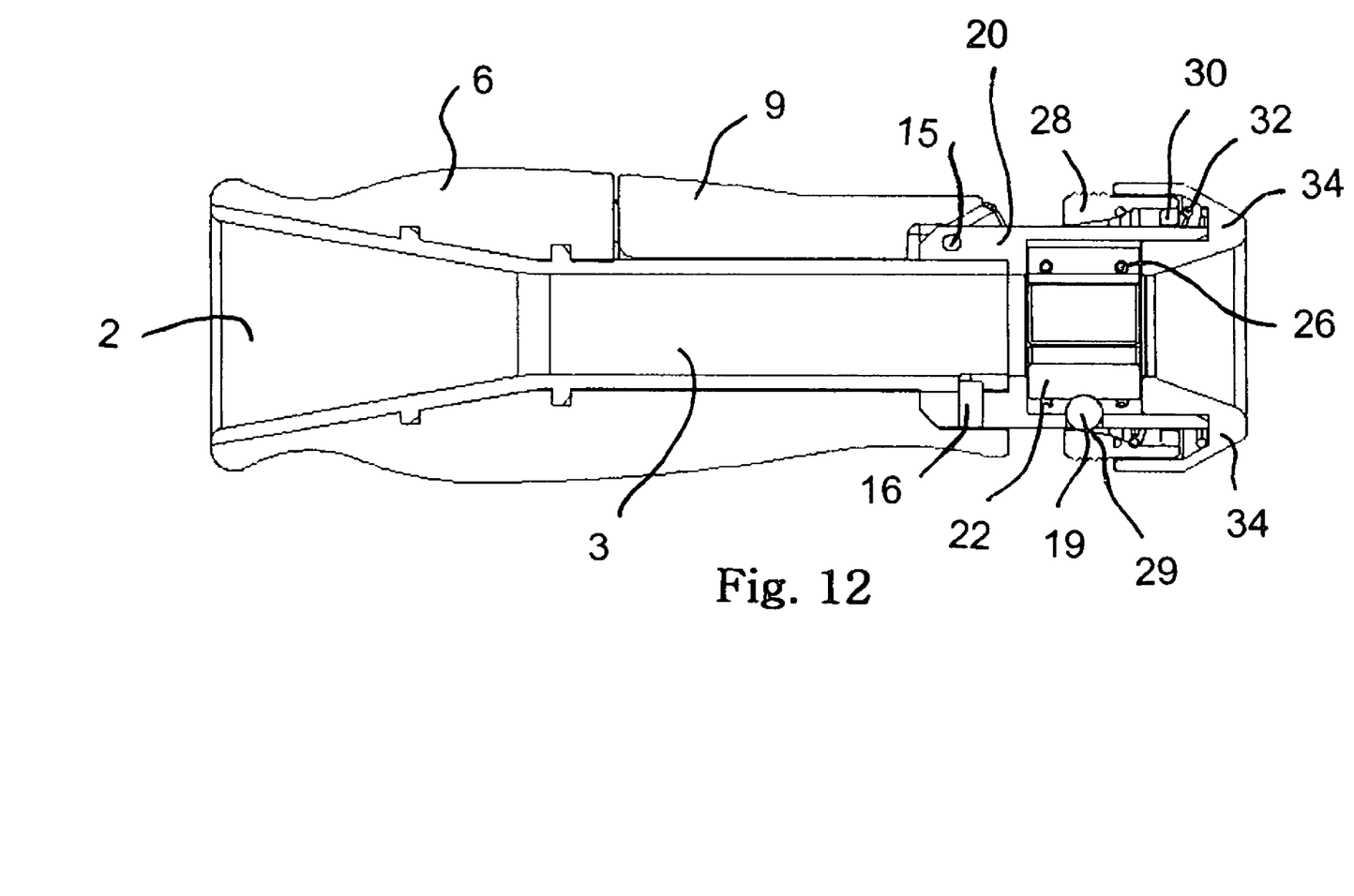
FIG. 12 is a longitudinal-sectional view of the instrument holder with the trigger depressed in the locked condition.
Figure 13:
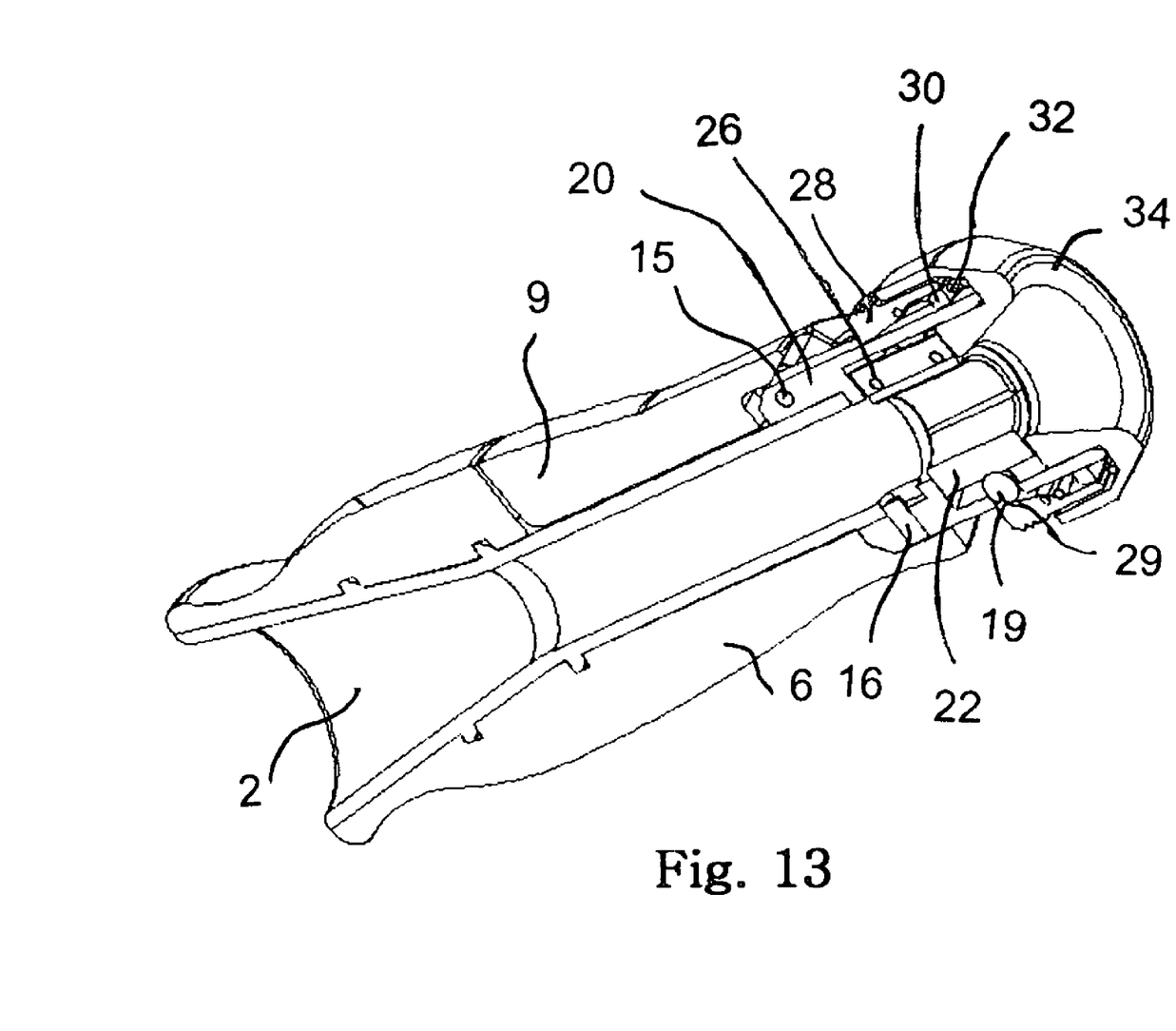
FIG. 13 is a fragmentary, perspective longitudinal-sectional view of the instrument holder with the trigger depressed in the locked condition.

FIGS. 12 and 13 show the trigger fully depressed and therefore the clamping shoes 22, 23, 24 fully displaced radially inwardly against the instrument 40, due to the cam surface 29 being fully run up over the ball bearings 19. Upon release of the trigger 9, the spring 32 would once again push the cam 28 proximally and the ball bearings 19 would roll along the cam surface 29 and be pushed radially outwardly again by the springs 26 and the clamping shoes 22, 23, 24, while releasing the instrument 40.

The invention claimed is:

1. An instrument holder, comprising:
a grip to be held by an operator for guiding an instrument;
an actuator to be activated by the operator;
a first biasing device exerting a first force; and
a clamp including:
   a plurality of clamping shoes disposed to surround the instrument; and
   a plurality of second biasing devices, each of the second biasing devices being disposed between a respective pair of said clamping shoes and exerting a second force, the clamping shoes being biased by the first and second forces of respective first and second biasing devices radially away from the instrument, the clamping shoes operable to be moved by said actuator against the first and second forces of said respective first and second biasing devices radially inward toward the instrument.

2. The instrument holder according to claim 1, wherein:
said first biasing device is a spring, and
said actuator is a trigger being pivoted away from said grip by said spring and being pivoted toward said grip by the operator for engaging the instrument with said clamp.

3. The instrument holder according to claim 2, which further comprises a cam being moved by said trigger for displacing said clamping shoes toward the instrument and being moved by said spring for displacing said clamping shoes away from the instrument.

4. The instrument holder according to claim 3, which further comprises ball bearings, said cam having a cam surface on which said ball bearings ride toward and away from said clamping shoes upon movement of said cam.

5. The instrument holder according to claim 4, which further comprises a clamp body having holes formed therein in which said ball bearings move toward and away from said clamping shoes.

6. The instrument holder according to claim 3, which further comprises a nose, said spring being biased between said nose and said cam.

7. The instrument holder according to claim 3, which further comprises a cam ring disposed within said cam.

8. The instrument holder according to claim 5, which further comprises a grip tube extended through said grip, one dowel pin on which said trigger pivots on said grip, and another dowel pin disposed between said clamp body and said grip tube, perpendicular to said one dowel.

9. The instrument holder according to claim 2, which further comprises cam lock springs each being disposed between a respective two of said clamping shoes.

10. The instrument holder according to claim 5, wherein said clamping shoes each have a protrusion being engaged by a respective one of said ball bearings.

11. The instrument holder according to claim 8, which further comprises set screws disposed between said clamp body and said grip tube.

12. The instrument holder according to claim 1, wherein said actuator and said first biasing device allow infinite adjustment of contact between said clamp and the instrument by the operator.

13. A method for operating an instrument holder, the method comprising the following steps:
  guiding an instrument in a grip to be held by an operator;
  providing an actuator to be activated by the operator;
  exerting a first force against activation of the actuator with a first biasing device;
  providing a clamp for engaging the instrument, the clamp including a plurality of clamping shoes disposed to surround the instrument and a plurality of second biasing devices, each second biasing device being disposed between a respective pair of said clamping shoes and exerting a second force, the clamping shoes being biased by the first and second forces of respective first and second biasing devices radially away from the instrument;
  activating the actuator against the first force of the first biasing device, which activation moves the clamping shoes against the second force of the second biasing devices radially inward toward the instrument; and
  moving the clamping shoes radially away from the instrument with the first and second forces of respective first and second biasing devices.

14. The method according to claim 13, wherein:
the first biasing device is a spring, and
the actuator is a trigger being pivoted away from the grip by the spring and being pivoted toward the grip by the operator for engaging the instrument with the clamp.

15. The method according to claim 14, which further comprises
  moving a cam with the trigger for displacing the clamping shoes toward the instrument, and
  moving the cam with the spring for displacing the clamping shoes away from the instrument.

16. The method according to claim 15, which further comprises biasing the clamping shoes away from each other with cam lock springs.

17. The method according to claim 15, which further comprises biasing the spring between a nose and the cam.

18. The method according to claim 13, which further comprises infinitely adjusting contact between the clamp and the instrument with the actuator and the first and second biasing devices.

19. The instrument holder according to claim 1, wherein said clamp is moved by said first and second biasing devices away from the instrument automatically upon releasing said actuator.

20. The method according to claim 13, which further comprises moving the clamp away from the instrument with the first and second biasing devices automatically upon releasing the actuator.

* * * * *